United States Patent [19]

Moseley et al.

[11] Patent Number: 5,610,159

[45] Date of Patent: Mar. 11, 1997

[54] N-OXIDES OF MORPHOLINE DERIVATIVES AND THEIR USE AS THERAPEUTIC AGENTS

[75] Inventors: Jonathan D. Moseley, Bristol; Christopher J. Swain, Duxford; Brian J. Williams, Great Dunmow, all of England

[73] Assignee: Merck Sharp & Dohme Limited, Hoddesdon, England

[21] Appl. No.: 668,592

[22] Filed: Jun. 19, 1996

[30] Foreign Application Priority Data

Jun. 28, 1995 [GB] United Kingdom ............ 9513118

[51] Int. Cl.$^6$ .................. A61K 31/535; C07D 413/06
[52] U.S. Cl. .................. 514/236.2; 514/235.8; 544/132; 544/139
[58] Field of Search .................. 344/132, 139; 514/235.8, 236.2

[56] References Cited

U.S. PATENT DOCUMENTS 5,457,107 10/1995 Kaufman .................. 514/236.2

FOREIGN PATENT DOCUMENTS 0577394 1/1994 European Pat. Off. .
WO95/16679 6/1995 WIPO .

Primary Examiner—Robert W. Ramsuer
Attorney, Agent, or Firm—J. Eric Thies; David L. Rose

[57] ABSTRACT

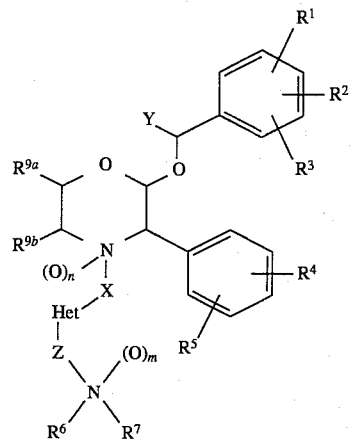

The present invention relates to morpholine derivatives of the formula (I) and pharmaceutically acceptable salts thereof wherein $R^1$, $R^2$, $R^3$, $R^4$, $R^5$, $R^6$, $R^7$, $R^{9a}$, $R^{9b}$, X, Y, Z and Het are as defined in the specification;

m is 0 or 1; and n is 0 or 1, where the sum total of n+m is 1 or 2.

The compounds are of particular use in the treatment of pain, inflammation, migraine, emesis and postherpetic neuralgia.

19 Claims, No Drawings

N-OXIDES OF MORPHOLINE DERIVATIVES AND THEIR USE AS THERAPEUTIC AGENTS

This invention relates to a class of morpholine derivatives which are useful as tachykinin antagonists. More particularly, this invention relates to the N-oxides of a class of morpholine derivatives which contain an amine-substituted azo-heterocyclic moiety.

The tachykinins are a group of naturally occurring peptides found widely distributed throughout mammalian tissues, both within the central nervous system and in peripheral nervous and circulatory systems.

The tachykinins are distinguished by a conserved carboxyl-terminal sequence:

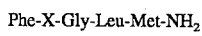

Phe-X-Gly-Leu-Met-NH$_2$

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the NK$_1$, NK$_2$ and NK$_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-refiexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, *Ciba Foundation Symposium* 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al in *Science* (1984) 226, 547–549]. Tachykinins have also been implicated in gastrointestinal (GI) disorders and diseases of the GI tract such as inflammatory bowel disease [Mantyh et al in *Neuroscience* (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet*, 11 Nov. 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol. Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *Proc. Natl. Acad. Sci., USA* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster C.I.N.P. XVIIIth Congress, 28th Jun.–2nd Jul. 1992], and in disorders of bladder function such as bladder detrusor hyper-refiexia (*The Lancet*, 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

European patent specification no. 0 577 394 (published 5th Jan. 1994) discloses morpholine and thiomorpholine tachykinin receptor antagonists of the general formula

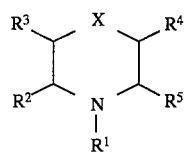

wherein R$^1$ is a large variety of substituents;

R$^2$ and R$^3$ are inter alia hydrogen;

R$^4$ is inter alia

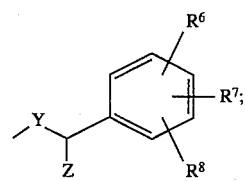

R$^5$ is inter alia optionally substituted phenyl;

R$^6$, R$^7$ and R$^8$ are a variety of substituents;

X is O, S, SO or SO$_2$;

Y is inter alia O; and

Z is hydrogen or C$_{1-4}$alkyl.

We have now found a further class of non-peptides which are potent antagonists of tachykinins, especially of substance P.

It is desirable that compounds may be administered orally and by injection. Certain compounds have now been discovered which act as potent non-peptide tachykinin antagonists and which, by virtue of their advantageous aqueous solubility, are particularly easily formulated for administration by both the oral and injection routes, for example in aqueous media.

The present invention provides compounds of the formula (I):

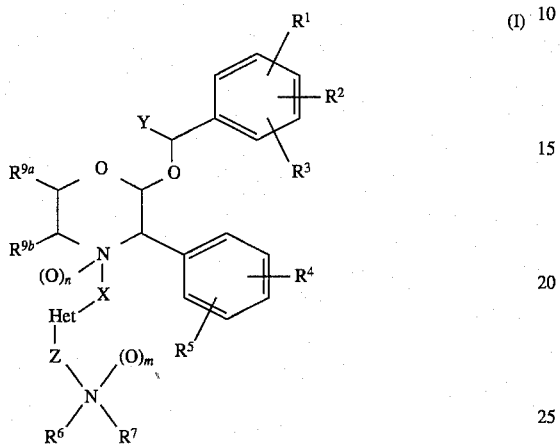

wherein $R^1$ is hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$akynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, $CF_3$, $OCF_3$ or $C_{1-6}$alkoxy substituted by $C_{1-4}$alkoxy;

$R^3$ is hydrogen, halogen, $CF_3$ or $OCF_3$;

$R^4$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, $C_{1-6}$alkoxy substituted by $C_{1-4}$alkoxy or $CF_3$;

$R^6$ is hydrogen, $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxy;

$R^7$ is hydrogen, $C_{1-4}$alkyl, $C_{3-7}$cycloalkyl, $C_{3-7}$cycloalkyl$C_{1-4}$alkyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;

or $R^6$ and $R^7$, together with the nitrogen atom to which they are attached, form a saturated or partially saturated heterocyclic ring of 4 to 7 ring atoms, which ring may optionally contain in the ring one oxygen or sulphur atom or a group selected from $NR^8$, $S(O)$ or $S(O)_2$ and which ring may be optionally substituted by one or two groups selected from hydroxy, $C_{1-4}$alkyl, hydroxy$C_{1-4}$alkyl, $C_{1-4}$alkoxy$C_{1-4}$alkyl, oxo, $COR^a$ or $CO_2R^a$ where $R^a$ is as previously defined;

or $R^6$ and $R^7$ together with the nitrogen atom to which they are attached, form a non-aromatic azabicyclic ring system of 6 to 12 ring atoms;

or Z, $R^6$ and the nitrogen atom to which are attached form a heteroaliphatic ring of 4 to 7 ring atoms which may optionally contain an oxygen ring atom;

$R^8$ is hydrogen, $C_{1-4}$alkyl, hydroxy$C_{1-4}$alkyl or $C_{1-4}$alkoxy$C_{1-4}$alkyl;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

Het is a 5- or 6-membered heterocyclic ring containing 2 or 3 nitrogen atoms optionally substituted by =O, =S or a $C_{1-4}$alkyl group;

X is an alkylene chain of 1 to 4 carbon atoms optionally substituted by oxo;

Y is a $C_{1-4}$alkyl group optionally substituted by hydroxy;

Z is $C_{1-6}$alkylene or $C_{3-7}$cycloalkylene;

m is 0 or 1; and n is 0 or 1, where the sum total of n+m is 1 or 2;

and pharmaceutically acceptable salts thereof.

According to an alternative aspect of the present invention, $R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl; $R^2$ is hydrogen, halogen, $C_{1-6}$alkyl, $C_{1-6}$alkoxy substituted by $C_{1-4}$alkoxy or $CF_3$; and $R^3$ is hydrogen, halogen or $CF_3$.

A preferred class of compounds of formula (I) is that wherein $R^1$ is hydrogen, $C_{1-4}$alkyl, $C_{1-4}$alkoxy, halogen or $CF_3$.

Another preferred class of compounds of formula (I) is that wherein $R^2$ is hydrogen, $C_{1-4}$alkyl, $C_{1-4}$alkoxy, halogen or $CF_3$.

Also preferred is the class of compounds of formula (I) wherein $R^3$ is hydrogen, fluorine, chlorine or $CF_3$.

A particularly preferred class of compounds of formula (I) is that wherein $R^1$ is fluorine, chlorine or $CF_3$.

Another particularly preferred class of compounds of formula (I) is that wherein $R^2$ is hydrogen, fluorine, chlorine or $CF_3$.

Also particularly preferred is the class of compounds of formula (I) wherein $R^3$ is hydrogen, fluorine, chlorine or $CF_3$.

Preferably $R^1$ and $R^2$ are in the 3 and 5 positions of the phenyl ring.

More preferably $R^1$ is 3-fluoro or 3-$CF_3$.

More preferably $R^2$ is 5-fluoro or 5-$CF_3$.

More preferably $R^3$ is hydrogen.

Most preferably $R^1$ is 3-F or 3-$CF_3$, $R^2$ is 5-$CF_3$ and $R^3$ is hydrogen.

A further preferred class of compound of formula (I) is that wherein $R^4$ is hydrogen.

Another preferred class of compounds of formula (I) is that wherein $R^5$ is hydrogen, fluorine, chlorine or $CF_3$.

Preferably $R^4$ is hydrogen and $R^5$ is hydrogen or 4-fluoro.

Also preferred is the class of compounds of formula (I) wherein $R^{9a}$ and $R^{9b}$ are each independently hydrogen or methyl. Preferably $R^{9a}$ is hydrogen. Preferably $R^{9b}$ is hydrogen. Most preferably $R^{9a}$ and $R^{9b}$ are both hydrogen.

A further preferred class of compounds of formula (I) is that wherein m is 1.

From the foregoing it will be appreciated that a particularly apt sub-group of compounds of this invention are those of the formula (Ia) and pharmaceutically acceptable salts thereof:

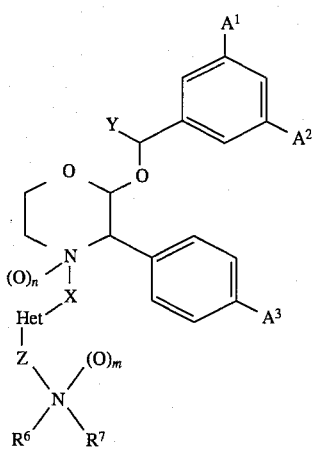

(Ia)

wherein

A¹ is fluorine or CF₃;

A² is fluorine or CF₃;

A³ is fluorine or hydrogen;

and $R^6$, $R^7$, X, Y, Z, Het, m and n are as defined in relation to formula (I).

A preferred group Y for compounds of the formulae (I) or (Ia) is the $C_{1-4}$alkyl group, especially the methyl group.

Where the group $NR^6R^7$ forms a saturated heterocylic ring of 4 to 7 ring atoms which may optionally contain in the ring one oxygen or sulphur atom or a group selected from $NR^8$, S(O) or S(O)₂, suitable heterocylic groups include azetidinyl, pyrrolidino, piperidino, homopiperidino, piperazino, N-methylpiperazino, morpholino and thiomorpholino.

Suitable substituents on the saturated heterocyclic ring include $CH_2OH$, $CH_2OCH_3$, oxo, CHO, $CO_2H$, $CO_2CH_3$, and $CO_2CH_2CH_3$.

When used herein the term "halogen" means fluorine, chlorine, bromine and iodine. The most apt halogen are fluorine and chlorine of which fluorine is preferred.

When used herein the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The term "alkenyl" as a group or part of a group means that the group is straight or branched and contains at least one double bond. Examples of suitable alkenyl groups include vinyl and allyl.

The term "alkynyl" as a group or part of a group means that the group is straight or branched and contains at least one triple bond. An example of a suitable alkynyl group is propargyl.

Suitable cycloalkyl and cycloalkyl-alkyl groups include cyclopropyl, cyclobutyl, cyclopentyl, cyclohexyl, cyclopropylmethyl and cyclobutylmethyl.

Where the group $NR^6R^7$ represents a heteroaliphatic ring of 4 to 7 ring atems and said ring is partially saturated, a particularly preferred group is 3-pyrroline.

Where the group $NR^6R^7$ represents a non-aromatic azabicyclic ring system, such a system may contain between 6 and 12, and preferably between 7 and 10, ring atoms.

Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^7$ represents a $C_{2-4}$alkyl group substituted by a 5 or 6 membered heteroaliphatic ring containing one or two heteroatoms selected from N, O and S, suitable rings include pyn-olidino, piperidino, piperazino, morpholino, or thiomorpholino. Particularly preferred are nitrogen containing heteroaliphatic rings, especially pyrrolidino and morpholino rings.

Particularly apt values for X for compounds of the formulae (I) or (Ia) include $CH_2$, $CH(CH_3)$ and $CH_2CH_2$ of which the $CH_2$ group is preferred.

Favourably Her is a 5-membered ring.

In particular, Her may represent a heterocyclic ring selected from:

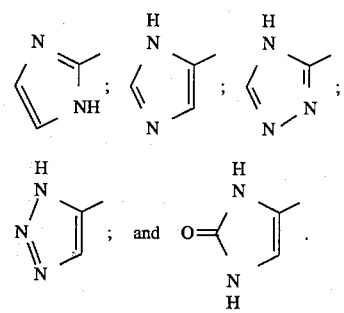

Particularly preferred heterocyclic rings represented by Het-$ZN(O)_mR^6R^7$ are selected from:

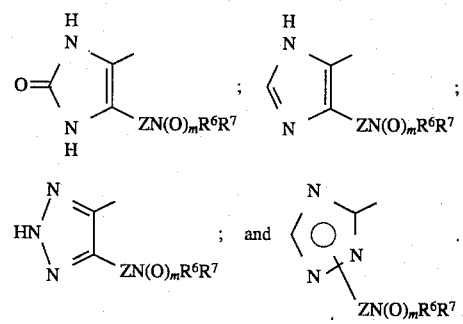

Most especially, Het-$ZN(O)_mR^6R^7$ may represent a heterocyclic ring selected from:

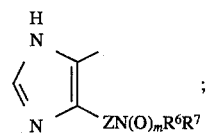

-continued

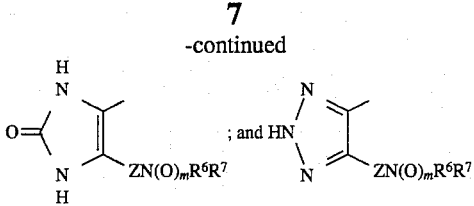

A particularly preferred heterocyclic ring represented by Het-ZN(O)$_m$R$^6$R$^7$ is:

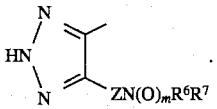

One favoured group of compounds of this invention are of the formula (Ib) and pharmaceutically acceptable salts thereof:

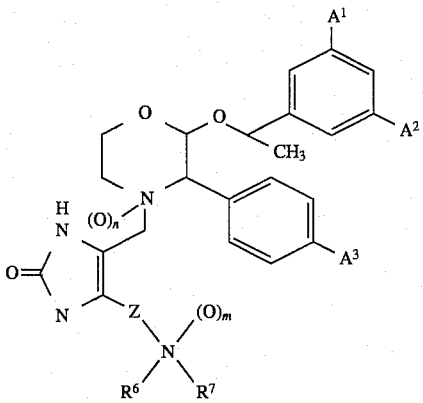

(Ib)

wherein A$^1$, A$^2$ and A$^3$ are defined in relation to formula (Ia) and wherein Z, R$^6$, R$^7$, m and n are as defined in relation to formula (I).

Another favoured group of compounds of the present invention are of the formula (Ic) and pharmaceutically acceptable salts thereof:

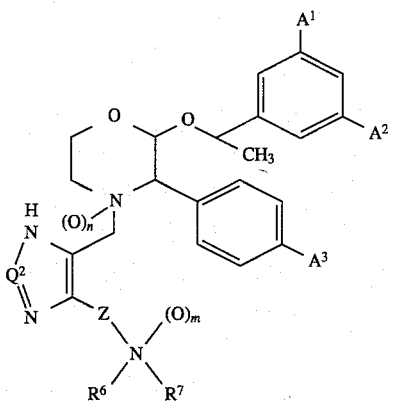

(Ic)

wherein A$^1$, A$^2$ and A$^3$ are defined in relation to formula (Ia), Q$^2$ is CH or N and Z, R$^6$, R$^7$, m and n are as defined in relation to formula (I).

With respect to compounds of the formulae (I), (Ia), (Ib) and (Ic), Z may be a linear, branched or cyclic group. Favourably Z contains 1 to 4 carbon atoms and most favourably 1 or 2 carbon atoms. A particularly favourable group Z is CH$_2$.

With respect to compounds of the formulae (I), (Ia), (Ib) and (Ic), R$^6$ may aptly be a C$_{1-4}$alkyl group or a C$_{2-4}$alkyl group substituted by a hydroxyl or C$_{1-2}$alkoxy group, R$^7$ may aptly be a C$_{1-4}$alkyl group or a C$_{1-4}$alkyl group substituted by a hydroxyl or C$_{1-2}$alkoxy group, or R$^6$ and R$^7$ may be linked so that, together with the nitrogen atom to which they are attached, they form an azetidinyl, pyrrolidinyl, piperidyl, morpholino, thiomorpholino, piperazino or piperazino group substituted on the nitrogen atom by a C$_{1-4}$alkyl group or a C$_{2-4}$alkyl group substituted by a hydroxy or C$_{1-2}$alkoxy group.

Particularly suitable moieties ZNR$^6$R$^7$ include those wherein Z is CH$_2$ or CH$_2$CH$_2$ and NR$^6$R$^7$ is amino, methylamino, dimethylamino, diethylamino, azetidinyl, pyrrolidino and morpholino.

Further preferred moieties represented by ZNR$^6$R$^7$ are those wherein Z is CH$_2$ or CH$_2$CH$_2$, R$^6$ represents hydrogen, C$_{1-4}$alkyl or C$_{3-6}$cycloalkyl and R$^7$ is C$_{2-4}$alkyl substituted by one or two substituents selected from hydroxy, C$_{1-2}$alkoxy, azetidinyl, pyrrolidino, piperidino, morpholino or thiomorpholino.

In particular, Z is preferably CH$_2$ and NR$^6$R$^7$ is preferably dimethylamino, azetidinyl or pyrrolidino, especially dimethylamino.

According to a further aspect of the present invention, or particularly preferred class of compound is that represented by fomula (Id) and pahramceutically acceptable salts thereof:

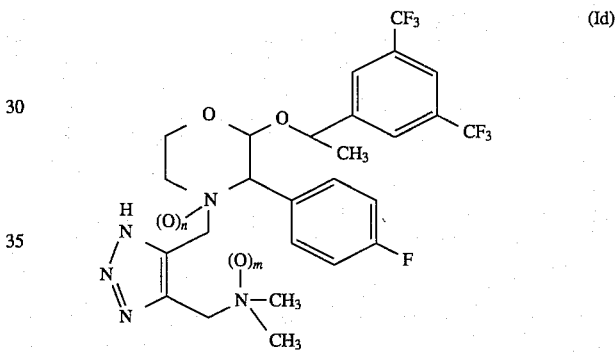

(Id)

wherein m and n are as defined in relation to formula (I).

Specific compounds within the scope of the present invention include:
2-(R)-(1-(R)-(3,5-bis(trifluoromethyl)phenyl)ethoxy)4-(5-(N,N-dimethylamino(N-oxide)methyl)-1,2,3-triazol-4-yl)methyl-3-(S)-(4-fluorophenyl)morpholine;
2-(R)-(1-(R)-(3,5-bis(trifluoromethyl)phenyl)ethoxy)-4-(5-(N,N-dimethylaminomethyl)-1,2,3-triazol-4-yl)methyl-3-(S)-(4-flyuorophenyl)morpholine N-oxide;
2-(R)-(1-(R)-(3,5-bis(trifluoromethyl)phenyl)ethoxy)-4-(5-(N,N-dimethylamino(N-oxide)methyl)-1,2,3-triazol-4-yl)methyl-3-(S)-(4-fluorophenyl)morpholine N-oxide;
3-(S)-(4-fluorophenyl)-2-(R)-(1-(R)-(3-methylthio-5-(trifluoromethyl)phenyl)ethoxy)-4-(5-pyrrolidinomethyl-1,2,3-triazol-4-yl)methylmorpholine N-oxide;
3-(S)-(4-fluorophenyl)-2-(R)-(1-(R)-(3-methylthio-5-(trifluoromethyl)phenyl)ethoxy)-4-(5-pyrrolidino(N-oxide)methyl-1,2,3-triazol-4-yl)methylmorpholine N-oxide;
and pharmaceutically acceptable salts thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionolity.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I), (Ia), (Ib), (Ic) and (Id) will have the 2- and 3- substituent cis and the preferred stereochemistry at the 2-position is that possessed by the compound of Example 1 (i.e. 2-(R)-), the preferred stereochemistry of the 3-position is that possessed by the compound of Example 1 (i.e. 3-(S)), and the preferred stereochemistry of the carbon to which the group Y is attached is either (R) when Y is $C_{1-4}$alkyl (e.g. methyl) or (S) when Y is $C_{1-4}$alkyl substituted by hydroxy (e.g. $CH_2OH$). Thus for example as shown in formula (Ie)

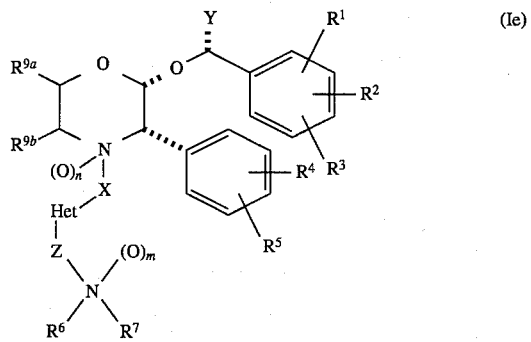

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric adds with such materials as shellac, cetyl alcohol and cellulose acetate.

The liquid forms in which the novel compositions of the present invention may be incorporated for administration orally or by injection include aqueous solutions, suitably flavored syrups, aqueous or off suspensions, and flavored emulsions with edible offs such as cottonseed off, sesame oil, coconut off or peanut off, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Preferred compositions for administration by injection include those comprising a compound of formula (I), as the active ingredient, in association with a surface-active agent (or wetting agent or surfactant) or in the form of an emulsion (as a water-in-off or off-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will convenienfiy comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention luther provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrige's disease) and other neuropathological disorders such as peripheral neuropathy, for example AIDS related neuropathy, diabetic and chemotherapy-induced neuropathy, and postherpetic and other neuralgias; neuronal damage, such as cerebralischemic damage and cerebral edema in cerebrovascular disorders; small cell carcinomas such as small cell lung cancer; respiratory diseases, particularly those associated with excess mucus secretion such as chronic obstructive airways disease, bronchopneumonia, chronic bronchitis, asthma, and bronchospasm; airways diseases modulated by neurogenic inflammation; diseases characterised by neurogenic mucus secretion, such as cystic fibrosis; diseases associated with decreased glandular secretions, including lacrimation, such as Sjogren's syndrome, hyperlipoproteinemias IV and V, hemocromatosis, sarcoidosis, and amyloidosis; inflammatory diseases such as inflammatory bowel disease, psoriasis, fibrositis, ocular inflammation, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders including the withdrawal response produced by chronic treatment with, or abuse of, drugs such as benzodiazepines, opiates, cocaine, alcohol and nicotine; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders, including inflammatory disorders, and diseases of the GI tract, such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed, post-operative, late phase or anticipatory emesis such as emesis induced by chemotherapy, radiation, toxins, vital or bacterial infections, pregnancy, vestibular disorders, motion, surgery, migraine, opioid analgesics, and variations in intercranial pressure, in particular, for example, drug or radiation induced emesis or post-operative nausea and vomiting; disorders of bladder function such as cystitis, bladder detrusor hyper-refiexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

Hence, the compounds of the present invention may be of use in the treatment of physiological disorders associated with excessive stimulation of tachykinin receptors, especially neurokinin-1 receptors, and as neurokinin-1 antagonists for the control and/or treatment of any of the aforementioned clinical conditions in mammals, including humans.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed, post-operative, late phase or anticipatory emesis, such as emesis or nausea induced by chemotherapy, radiation, toxins, such as metabolic or microbial toxins, viral or bacterial infections, pregnancy, vestibular disorders, motion, mechanical stimulation, gastrointestinal obstruction, reduced gatrointestinal motility, visceral pain, psychological stress or disturbance, high altitude, weightlesshess, opioid analgesics, intoxication, resulting for example from consumption of alcohol, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *"Nausea and*

*Vomiting: Recent Research and Clinical Advances*", Eds. J. Kuucharczyk et al, CRC Press Inc., Boca Raton, Fla., U.S.A. (199 1) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarb azine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABA$_B$ receptor agonists such as baclofen. Additionally, a compound of formula (I) may be administered in combination with an antiinflammatory corticosteroid, such as dexamethasone, triamcinolone, triamcinolone acetonide, fiunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$, agonists, especially sumatriptan.

Likewise, for the treatment of behavioural hyperalgesia, a compound of the present invention may be used in conjunction with an 3ntagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.00 1 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to one general process, the compounds of formula (I) may be prepared from compounds of formula (II)

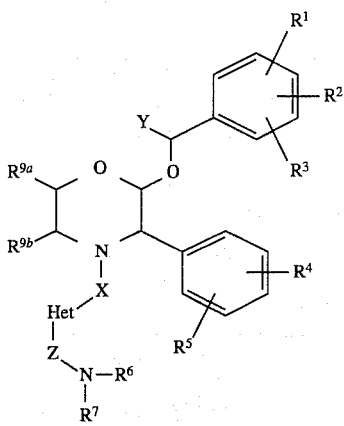

(II)

by oxidation of one or both of the nitrogen atoms drawn in formula (II).

The oxidation reaction may be effected using hydrogen peroxide, an alkyl peroxide such as t-butylperoxide or a peroxy acid (peracid) such as m-chlorop erbenzoic acid or peracetic acid. Hydrogen peroxide is particularly preferred. The reaction is conveniently effected at room temperature in a solvent such as an ether, for example, tetrahydrofuran, acetonitrile or a chlorinated hydrocarbon, for example, dichloromethane, or an off, for example, soya bean oil.

Where oxidation of the morpholine nitrogen is desired, the reaction is conveniently effected in acidic conditions, for example, using hydrogen peroxide in acetic acid.

Where oxidation of the amine moiety $NR^6R^7$ is desired, neutral conditions are preferred, for example, using hydrogen peroxide in soya bean oil.

Compounds of formula (II) may be prepared by a variety of methods, thus, according to intermediate process (A), the compounds of formula (II) may be prepared from compounds of formula (IIIa)

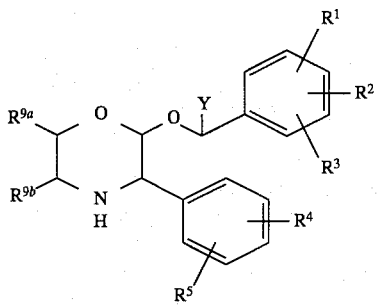

(IIIa)

wherein $R^1$, $R^2$, $R^3$, $R^4$, $R^5$ and Y are as defined in relation to formula (I) by reaction with a compound of formula (IIIb):

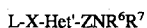

(IIIb)

where X is as defined in relation to formula (I), Het' is as defined for the group Het in relation to formula (I) or a precursor therefor and L is a leaving group for example a halogen atom such as bromine or chlorine; and, if Het' is a precursor group, converting it to a group Het (in which process any reactive group may be protected and thereafter deprotected ff desired).

This reaction may be performed in conventional manner, for example in an organic solvent such as dimethylformamide in the presence of an acid acceptor such as potassium carbonate.

According to another process (B), compounds of formula (II) wherein Het represents 1,2,3-triazol-4-yl substituted by $CH_2NR^6R^7$, and X is —$CH_2$—, may be prepared by reaction of a compound of formula (IV)

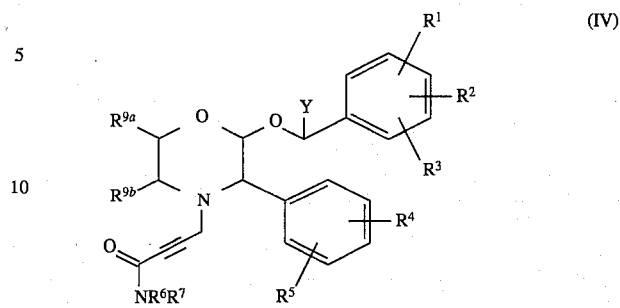

(IV)

with an azide, for example, sodium azide in a suitable solvent such as dimethylsulphoxide at a temperature of between 40° C. and 100° C., followed by reduction of the carbonyl group adjacent to —$NR^6R^7$ using a suitable reducing agent such as lithium aluminjure hydride at at a temperature between −10° C. and room temperature, conveniently at room temperature.

Alternatively, according to a process (C), compounds of formula (II) wherein Het represents 1,2,3-triazol-4-yl substituted by $CH_2NR^6R^7$, and X is —$CH_2$—, may be prepared by reaction of a compound of formula (V)

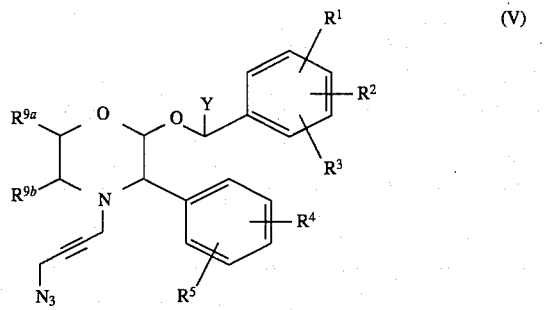

(V)

with an amine of formula $NHR^6R^7$, in a suitable solvent such as an ether, for example, dioxan, at elevated temperature, for example, between 50° C. and 100° C., in a sealed tube, or the like. This reaction is based upon that described in *Chemische Berichte* (1989) 122, p. 1963.

According to another process, (D), compounds of formula (II) wherein Het represents 1,3,5-triazine may be prepared by reaction of intermediates of formula (VI):

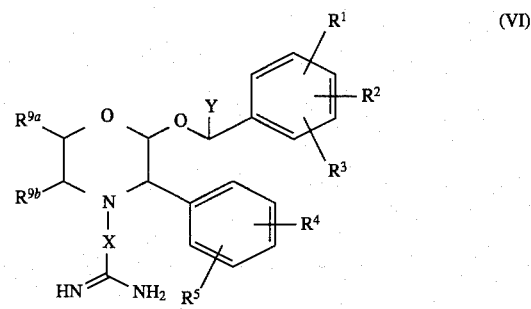

(VI)

with an appropriately substituted 1,3,5-triazine.

The reaction is conveniently effected in a suitable organic solvent, such as acetonitrile, at elevated temperature, such as 80°–90° C., preferably about 82° C.

According to a further process, (E), compounds of formula wherein Het represents 1,2,4-triazine may be prepared by reaction of intermediate of formula (VII) with a dicarbonyl compound of formula (VIII):

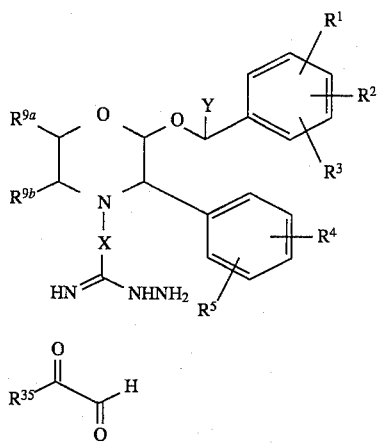

(VII)

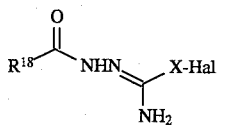

(VIII)

wherein $R^{35}$ represents the substituent $ZNR^6R^7$.

The reaction is conveniently effected in a suitable organic solvent, such as an ether, e.g. tetrahydrofuran, conveniently at ambient temperature.

According to a further process (F), compounds of formula (II) wherein Het represents a substituted 1,2,4-triazolyl group may be prepared by reaction of an intermediate of formula (III) with a compound of formula (IX)

(IX)

wherein X is as defined in relation to formula (I), Hal is a halogen atom, for example, bromine, chlorine or iodine and $R^{18}$ is H, $CONH_2$ or $OCH_3$ (which is converted to an oxo substituent under the reaction conditions), in the presence of a base, followed where necessary by conversion to a compound of formula (I), for example, by reduction of the $CONH_2$ group to $CH_2NH_2$.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as about 140° C.

A suitable reducing agent for the group $CONH_2$ is lithium aluminium hydride, used at between −10° C. and room temperature.

According to another process, (G), compounds of formula (II) wherein Het represents thioxotriazolyl may be prepared from intermediates of formula (X)

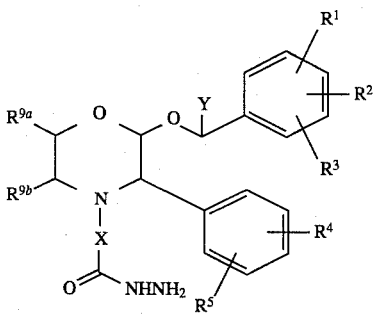

(X)

by reaction with a compound of formula HNCS, in the presence of a base.

Suitable bases of use in the reaction include organic bases such as, for example, 1,8-diazabicyclo[5.4.0]undec-7-ene (DBU). The reaction is conveniently effected in a suitable organic solvent, such as alcohol, e.g. butanol.

Further details of suitable procedures will be found in the accompanying Examples.

Intermediates of formula (IV) may be prepared from intermediates of formula (IIIa) by reaction with an acetylene compound of formula $HC{\equiv}C$—$CH_2$-Hal in the presence of a base such as potassium carbonate in a suitable solvent such as dimethylformamide, conveniently at room temperature, followed by reaction of the resultant acetylene intermediate with an amide of formula Hal-CO—$NR^6R^7$ in the presence of suitable catalysts including bis(triphenylphosphine) palladium(II) chloride, copper(I) iodide and triphenylphosphine in a suitable solvent such as triethylamine, preferably at reflux.

Intermediates of formula (V) may be prepared from a compound of formula (XI)

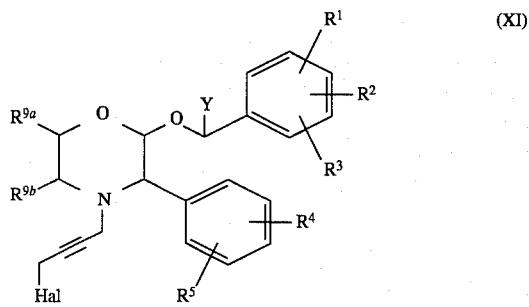

(XI)

wherein Hal is a halogen atom, for example, chlorine, bromine or iodine, especially chlorine, by reaction with an azide, for example, sodium azide in a suitable solvent such as dimethylsulphoxide at or below room temperature.

Compounds of formula (XI) may be prepared by a dropwise addition of an intermediate of formula (IIIa) to a dihaloacetylene of formula Hal-$CH_2$—$C{\equiv}C$—$CH_2$-Hal where each Hal is independently chlorine, bromine or iodine, especially chlorine. The reaction is conveniently effected in a suitable solvent such as dimethylformamide in the presence of a base such as potassium carbonate.

Intermediates of formula (VI) may be prepared from intermediates of formula (IIIa) by reaction with a compound of formula Hal-X—C(NH)$NH_2$, where Hal and X are as previously defined. Intermediates of formula (VII) may be prepared from intermediates of formula (IIIa) by reaction with a compound of formula Hal-X—C(NH)NHNH-Boc, wherein Hal and X are as previously defined and Boc stands for t-butoxycarbonyl, followed by deprotection under acidic conditions.

Compounds of formula (VIII) are commercially available or may be prepared from commercially available compounds by known methods. Compounds of formula (IX) may be prepared as described in *J. Med. Chem.*, (1984) 27, 849.

Intermediates of formula (X) may be prepared from the corresponding ester by treatment with hydrazine. The reaction is conveniently effected in a suitable organic solvent, such as an alcohol, for example, ethanol, at elevated temperature.

For compounds wherein Het is a heterocycle bearing the $ZNR^6R^7$ group where Z is $CH_2$, certain favoured compounds of formula (I) may be prepared from a corresponding compound with a hydrogen atom in place of the $ZNR^6R^7$. Thus, for example a compound of the formula (I) wherein Het is an imidazolinone group carrying a $CH_2NR^6R^7$ moiety may be prepared from a corresponding compound lacking the $CH_2NR^6R^7$ moiety by reaction with formaldehyde and an amine $NHR^6R^7$ under conventional Mannich reaction conditions, for example in methanol with heating. If desired a pre-formed reagent such as $R^6R^7N^+=CH_2.I^-$ may be employed and a tertiary amine such as triethylamine used as acid acceptor.

Alternatively a compound of formula (I) wherein Het is an imidazolinone group lacking a $CH_2NR^6R^7$ may be reacted with paraformaldehyde and an amine for example a secondary amine such as pyrrolidine to give a compound wherein the imidazolinone ring is substituted by $CH_2NR^6R^7$ where $R^6$, $R^7$ and the nitrogen atom to which they are attached form a heteroaliphatic ring of 4 to 7 ring atoms which may optionally contain an oxygen ring atom or a second nitrogen atom which will be part of a $NR^8$ moiety, where $R^8$ is as previously defined.

This reaction may be performed in a conventional manner, for instance, in a suitable solvent such as an alcohol, for example, methanol at an elevated temperature up to the boiling point of the solvent.

A further alternative method for the preparation of certain compounds of formula (II) involves the reaction of an intermediate of formula (IIIa) as defined above with one of the compounds of formula (XII):

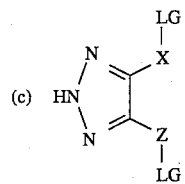

wherein each LG, which may be the same or different, is a leaving group, such as an alkyl- or arylsulphonyloxy group (e.g. mesylate or tosylate) or, in particular, a halogen atom, (e.g. bromine, chlorine or iodine) and X and Z are as defined in formula (I), followed by reaction of the resultant compound with an amine $NHR^6R^7$ to complete the $ZNR^6R^7$ moiety.

This reaction is conveniently effected in an organic solvent such as dimethylformamide in the presence of an acid acceptor such as potassium carbonate.

It will be appreciated that, where necessary, reactive groups may be protected, thus for example, the NH groups of an imidazolinone of formula (XIIa) may be protected by any suitable amine protecting group such as an acetyl group.

The compounds of the formula (IIIa) may be prepared as shown in the following Scheme in which $Ar^1$ represents the $R^1$, $R^2$, $R^3$ substituted phenyl group; $Ar^2$ represents the $R^4$, $R^5$ substituted phenyl group and Ph represents phenyl:

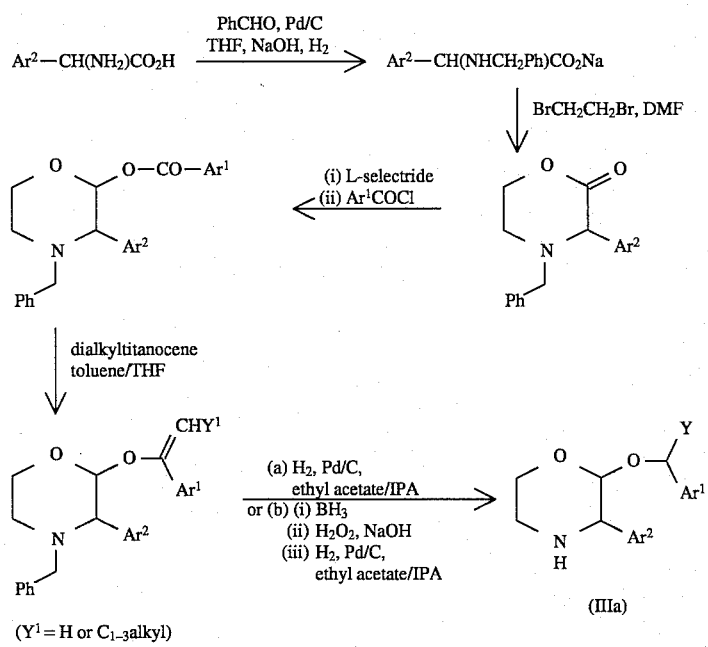

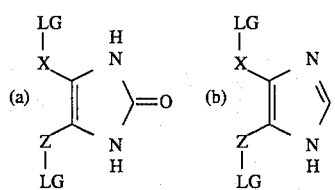

L-Selectride is lithium tri-sec-butylborohydride.

The following references describe methods which may be applied by the skilled worker to the chemical synthesis set forth above once the skilled worker has read the disclosure herein:

(I) D. A. Evans et al., *J. Am. Chem. Soc.*, (1990) 112, 4011.

(ii) I. Yanagisawa et al., *J. Med. Chem.*, (1984) 27, 849.

(iii) R. Duschinsky et al., *J. Am. Chem. Soc.*, (1948) 70, 657.

(iv) F. N. Tebbe et al., *J. Am. Chem. Soc.*, (1978)100, 3611.

(v) N. A. Petasis et al., *J. Am. Chem. Soc.*, (1990) 112, 6532.

(vi) K. Takai et al., *J. Org. Chem.*, (1987) 52, 4412.

The Examples disclosed herein produce predominently the preferred isomers. The unfavoured isomers are also produced as minor components. If desired they may be isolated and employed to prepare the various stereoisomers in conventional manner, for example chromatography using an appropriate column. However, the skilled worker will appreciate that although the Examples have been optimized to the production of the preferred isomers, variation in solvent, reagents, chromatography etc can be readily employed to yield the other isomers.

It will be appreciated that compounds of the formula (I) wherein Het contains an =O or =S substituent can exist in tautomeric forms. All such tautomeric forms and mixtures thereof are included within this invention. Most aptly the =O or =S substituent in Het is the =O substituent.

Where they are not commercially available, the intermediates of formula (III) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds or, in the case of prodrugs, the parent compounds, were found to be active with $IC_{50}$ at the $NK_1$ receptor of less than 100 nM on said test method.

The following Examples illustrate the preparation of compounds according to the present invention:

DESCRIPTION 1

(S)-(4-Fluorophenyl)glycine

Via Chiral Synthesis:

Step A: 3-(4-Fluorophenyl)acetyl-4-(S)-benzyl-2-oxazolidinone

An oven-dried, 1 L 3-necked flask, equipped with a septum, nitrogen inlet, thermometer, and a magnetic stirring bar, was flushed with nitrogen and charged with a solution of 5.09 g (33.0 mmol) of 4-fluorophenylacetic acid in 100 ml of anhydrous ether. The solution was cooled to −10° C. and treated with 5.60 ml (40.0 mmol) of triethylamine followed by 4.30 ml (35.0 mmol) of trimethylacetyl chloride. A white precipitate formed immediately. The resulting mixture was stirred at −10° C. for 40 minutes, then cooled to −78° C.

An oven-dried, 250 ml round bottom flask, equipped with a septum and a magnetic stirring bar, was flushed with nitrogen and charged with a solution of 5.31 g (30.0 mmol) of 4-(S)-benzyl-2-oxazolidinone in 40 ml of dry THF. The solution was stirred in a dry ice/acetone bath for 10 minutes, then 18.8 ml of 1.6M n-butyllithium solution in hexanes was slowly added. After 10 minutes, the lithiated oxazolidinone solution was added, via cannula, to the above mixture in the 3-necked flask. The cooling bath was removed from the resulting mixture and the temperature was allowed to rise to 0° C. The reaction was quenched with 100 ml of saturated aqueous ammonium chloride solution, transferred to a 1 l flask, and the ether and THF were removed in, vacuo. The concentrated mixture was partitioned between 300 ml of methylene chloride and 50 ml of water and the layers were separated. The organic layer was washed with 100 ml of 2N aqueous hydrochloric acid solution, 300 ml of saturated aqueous sodium bicarbonate solution, dried over magnesium sulfate and concentrated in vacuo. Flash chromatography on 400 g of silica gel using 3:2 v/v hexanes/ether as the eluant afforded 8.95 g of an oil that slowly solidified on standing. Recrystallisation from 10:1 hexanes/ether afforded 7.89 g (83%) of the title compound as a white solid: mp 64°–66° C. MS (FAB): m/z 314 (M$^+$+H, 100%), 177 (M-ArCH$_2$CO+H, 85%). 1H NMR (400 MHz, CDCl$_3$) δ2.76 (1H, dd, J=13.2, 9.2 Hz), 3.26 (dd, J=13.2, 3.2 Hz), 4.16–4.34 (4H, m), 4.65 (1H, m), 7.02–7.33 (9H, m).

Analysis Calcd. for $C_{18}H_{16}FNO_3$: C, 69.00; H, 5.15; N, 4.47; F, 6.06; Found: C, 68.86; H, 5.14; N, 4.48; F, 6.08%.

Step B: 3-((S)-Azido-(4-fluorophenyl))acetyl-4-(S)-benzyl-2-oxazolidinone

An oven-dried, 1 l 3-necked flask, equipped with a septum, nitrogen inlet, thermometer, and a magnetic stirring bar, was flushed with nitrogen and charged with a solution of 58.0 ml of 1M potassium bis(trimethylsilyl)amide solution in toluene and 85 ml of THF and was cooled to −78° C. An oven-dried 250 ml round-bottomed flask, equipped with a septum and a magnetic stirring bar, was flushed with nitrogen and charged with a solution of 7.20 g (23.0 mmol) of 3-(4-fluorophenyl)acetyl-4-(S)-benzyl-2-oxazolidinone (from Step A) in 40 ml of THF. The acyl oxazolidinone solution was stirred in a dry ice/acetone bath for 10 minutes, then transferred, via cannula, to the potassium bis(trimethylsilyl)amide solution at such a rate that the internal temperature of the mixture was maintained below −70° C. The acyl oxazolidinone flask was rinsed with 15 ml of THF and the rinse was added, via cannula, to the reaction mixture and the resulting mixture was stirred at −78° C. for 30 minutes. An oven-dried, 250 ml round-bottomed flask, equipped with a septum and a magnetic stirring bar, was flushed with nitrogen and charged with a solution of 10.89 g (35.0 mmol) of 2,4,6-triisopropylphenylsulfonyl azide in 40 ml of THF. The azide solution was stirred in a dry ice/acetone bath for 10 minutes, then transferred, via cannula, to the reaction mixture at such a rate that the internal temperature of the mixture was maintained below −70° C. After 2 minutes, the reaction was quenched with 6.0 ml of glacial acetic acid, the cooling bath was removed and the mixture was stirred at room temperature for 18 hours. The quenched reaction mixture was partitioned between 300 ml of ethyl acetate and 300 ml of 50% saturated aqueous sodium bicarbonate solution. The organic layer was separated, dried over magnesium sulfates, and concentrated in vacuo. Flash chromatography on 500 g of silica gel using 2:1 v/v, then 1:1 v/v hexanes/methylene chloride as the eluant afforded 5.45 g (67%) of the title compound as an oil. IR Spectrum (neat, cm$^-$): 2104, 1781, 1702. $^1$H NMR (400 MHz, CDCl$_3$) δ2.86 (1H, dd, J=13.2, 9.6 Hz), 3.40 (1H, dd, J=13.2, 3.2 Hz), 4.09–4.19 (2H, m), 4.62–4.68 (1H, m), 6.14 (1H, s), 7.07–7.47 (9H, m).

Analysis Calcd. for $C_{18}H_{15}FN_4O_3$: C 61.01; H, 4.27; N, 15.81; F, 5.36; Found: C, 60.99; H, 4.19; N, 15.80; F, 5.34%.

Step C: (S)-Azido-(4-fluorophenyl)acetic acid

A solution of 5.40 g (15.2 mmol) of 3-((S)-azido-(4-fluorophenyl))acetyl-4-(S)-benzyl-2-oxazolidinone (from Step B) in 200 ml of 3:1 v/v THF/water was stirred in an ice bath for 10 minutes. 1.28 g (30.4 mmol) of lithium hydroxide monohydrate was added in one portion and the resulting mixture was stirred cold for 30 minutes. The reaction mixture was partitioned between 100 ml of methylene chloride and 100 ml of 25% saturated aqueous sodium bicarbonate solution and the layers were separated. The aqueous layer was washed with 2×100 ml of methylene chloride and acidified to pH 2 with 2N aqueous hydrochloric acid solution. The resulting mixture was extracted with 2×100 ml of ethyl acetate; the extracts were combined, washed with 50 ml of saturated aqueous sodium chloride solution, dried over magnesium sulfates, and concentrated in vacuo to afford 2.30 g (77%) of the title compound as an oil that was used in the following step without further purification. IR Spectrum (neat, cm$^{-1}$): 2111, 1724. $^1$H NMR (400 MHz, CDCl$_3$) δ5.06 (1H, s), 7.08–7.45 (4H, m), 8.75 (1H, br s).

Step D: (S)-(4-Fluorophenyl)glycine

A mixture of 2.30 g (11.8 mmol) of (S)-azido-(4-fluorophenyl)acetic acid (from Step C), 2.50 mg 10% palladium on carbon catalyst and 160 ml 3:1 v/v water/acetic acid was stirred under an atmosphere of hydrogen for 18 hours. The reaction mixture was filtered through Celite and the flask and filter cake were rinsed well with about 1 liter of 3:1 v/v water/acetic acid. The filtrate was concentrated in vacuo to about 50 ml of volume. 300 ml of toluene was added and the mixture concentrated to afford a solid. The solid was suspended in 1:1 v/v methanol/ether, filtered and dried to afford 1.99 g (100%) of the title compound. $^1$H NMR (400 MHz, D$_2$O+NaOD) δ3.97 (1H, s), 6.77 (2H, app t, J=8.8 Hz), 7.01 (2H, app t, J=5.6 Hz).

Via Resolution:

Step A' (4-Fluorophenyl)acetyl chloride

A solution of 150 g (0.974 mol) of 4-(fluorophenyl)acetic acid and 1 ml of N,N-dimethylformamide in 500 ml of toluene at 40° C. was treated with 20 ml of thionyl chloride and heated to 40° C. An additional 61.2 ml of thionyl chloride was added dropwise over 1.5 hours. After the addition, the solution was heated at 50° C. for 1 hour, the solvent was removed in vacuo and the residual off was distilled at reduced pressure (1.5 mmHg) to afford 150.4 g (89.5%) of the title compound, bp=68°–70° C.

Step B': Methyl 2-bromo-3-(4-fluorophenyl)acetate

A mixture of 150.4 g (0.872 mol) of 4-(fluorophenyl)acetyl chloride (from Step A') and 174.5 g (1.09 mol) of bromine was irradiated at 40°–50° C. with a quartz lamp for 5 hours. The reaction mixture was added dropwise to 400 ml of methanol and the solution was stirred for 16 hours. The solvent was removed in vacuo and the residual off was distilled at reduced pressure (1.5 mmHg) to afford 198.5 g (92%) of the title compound, bp=106°–110° C.

Step C': Methyl (±)-(4-fluorophenyl)glycine

A solution of 24.7 g (0.1 mmol) of methyl 2-bromo-2-(4-fluorophenyl)acetate (from Step B') and 2.28 g (0.01 mol) of benzyl triethylammonium chloride in 25 ml of methanol was treated with 6.8 g (0.105 mol) of sodium azide and the resulting mixture was stirred for 20 hours at room temperature. The reaction mixture was filtered; the filtrate was diluted with 50 ml of methanol and hydrogenated in the presence of 0.5 g of 10% Pd/C at 50 psi for 1 hour. The solution was filtered and the solvent removed in vacuo. The residue was partitioned between 10% aqueous sodium carbonate solution and ethyl acetate. The organic phase was washed with water, saturated aqueous sodium chloride solution dried over magnesium sulfate and concentrated in vacuo to afford 9.8 g of the title compound as an oil.

Step D': Methyl (S)-(4-fluorophenyl)glycinate

A solution of 58.4 g of methyl (+) 4-(fluorophenyl)glycinate (from Step C') in 110 ml of 7:1 v/v ethanol/water was mixed with a solution of 28.6 g (0.0799 mol) of O,O'-(+)-dibenzoyltartaric acid ((+)-DBT) (28.6 g, 0.0799 mol) in 110 ml of 7:1 v/v ethanol:water and the resulting solution was allowed to age at room temperature. Ethyl acetate (220 ml) was added after crystallisation was complete and the resulting mixture was cooled to −20° C. and filtered to afford 32.4 g of methyl (S)-(4-fluorophenyl)glycinate, (+)-DBT salt (ee=93.2%). The mother liquors were concentrated in vacuo and the free base was liberated by partitioning between ethyl acetate and aqueous sodium carbonate solution. A solution of free base, so obtained, in 110 ml of 7:1 v/v ethanol/water was mixed with a solution of 28.6 g (0.0799 mol) of O,O'-(−)-dibenzoyltartaric acid ((−)-DBT) (28.6 g, 0.0799 mol) in 110 ml of 7:1 v/v ethanol:water and the resulting solution was allowed to age at room temperature. Ethyl acetate (220 ml) was added after crysallisation was complete and the resulting mixture was cooled to −20° C. and filtered to afford 47.0 g of methyl (R)-(4-fluorophenyl)glycinate, (−)-DBT salt (ee=75.8%). Recycling of the mother liquors and addition of (+)-DBT gave a second crop of 7.4 g of (S)-(4-fluorophenyl)glycinate, (+)-DBT salt (ee=96.4%). The two crops of the (S)-amino ester (39.8 g) were combined in 200 ml of 7:1 v/v ethano-water, heated for 30 minutes and cooled to room temperature. Addition of ethyl acetate, cooling, and filtration of forded 31.7 g of (S)-(4-fluorophenyl)glycinate, (+)-DBT salt (ee>98%). Enantiomeric excess was determined by chiral HPLC (Crownpak CR(+) 5% MeOH in aq HClO$_4$ pH2 1.5 ml/min 40° C. 200 nm).

A mixture of 17.5 g of (S)-(4-fluorophenyl)glycinate, (+)-DBT salt and 32 ml of 5.5N HCl (32 ml) was heated at reflux for 1.5 hours. The reaction mixture was concentrated in, vacuo and the residue was dissolved in 40 ml of water. The aqueous solution was washed (3×33 ml of ethyl acetate) and the layers were separated. The pH of the aqueous layer was adjusted to 7 using ammonium hydroxide and the precipitated solid was filtered to afford 7.4 g of the title compound (ee=98.8%).

DESCRIPTION 2

4-Benzyl-3-(S)-(4-fluorophenyl)-2-morpholinone

Step A: N-Benzyl-(S)-(4-fluorophenyl)glycine

A solution of 1.87 g (11.05 mmol) of (S)-(4-fluorophenyl)-glycine (from Description 1) and 1.12 ml (11.1 mmol) of benzaldehyde in 11.1 ml of 1N aqueous sodium hydroxide solution and 11 ml of methanol at 0° C. was treated with 165 mg (4.4 mmol) of sodium borohydride. The cooling bath was removed and the resulting mixture was stirred at room temperature for 30 minutes. Second portions of benzaldehyde (1.12 ml (11.1 mmol)) and sodium borohydride (165 mg (4.4 mmol) were added to the reaction mixture and stirring was continued for 1.5 hours. The reaction mixture was partitioned between 100 ml of ether and 50 ml of water and the layers were separated. The aqueous layer was separated and filtered to remove a small amount of insoluble material. The filtrate was acidified to pH 5 with 2N aqueous hydrochloric acid solution and the solid that had precipitated was filtered, rinsed well with water, then ether, and dried to afford 1.95 g of the title compound. $^1$H NMR (400 MHz, D$_2$O+NaOD) δ3.33 (2H, AB q, J=8.4 Hz), 3.85 (1H, s), 6.79–7.16 (4H, m).

Step B; 4-Benzyl-3-(S)-(4-fluorophenyl)-2-morpholinone

A mixture of 1.95 g (7.5 mmol) of N-benzyl (S)-(4-fluorophenyl)glycine, 3.90 ml (22.5 mmol) of N,N-diisopropyl-ethylamine, 6.50 ml (75.0 mmol) of 1,2-dibromoethane and 40 ml of N,N-dimethylformamide was stirred at 100° C. for 20 hours (dissolution of all solids occurred on warming). The reaction mixture was cooled and concentrated in vacuo. The residue was partitioned between 250 ml of ether and 100 ml of 0.5N potassium hydrogen sulfates solution and the layers were separated. The organic layer was washed with 100 ml of saturated aqueous sodium bicarbonate solution, 3×150 ml of water, dried over magnesium sulfate, and concentrated in vacuo. Flash chromatography on 125 g of silica gel using 3:1 v/v hexanes/ether as the eluant afforded 1.58 g (74%) of the title compound as an oil. $^1$H NMR (400 MHz, CDCl$_3$) δ2.65 (1H, dt, J=3.2, 12.8 Hz), 3.00 (1H, dt, J=12.8, 2.8 Hz), 3.16 (1H, d, J=13.6 Hz), 3.76 (1H, d, J=13.6 Hz), 4.24 (1H, s), 4.37 (1H, dt, J=13.2, 3.2 Hz), 4.54 (1H, dt, J=2.8, 13.2 Hz), 7.07–7.56 (9H, m).

DESCRIPTION 3

4-Benzyl-2-(R)-(3,5-bis(trifluoromethyl)benzoyloxy)-3-(S)-(4-fluorophenyl)morpholine A solution of 2.67 g (10.0 mmol) of 4-benzyl-3-(S)-(4-fluorophenyl)-2-morpholinone (Description 2) in 40 ml of dry THF was cooled to −78° C. The cold solution was treated with 12.5 ml of 1.0M L-Selectride® solution in THF, maintaining the internal reaction temperature below −70° C. The resulting solution was stirred cold for 45 minutes and the reaction was charged with 3.60 ml(20.0 mmol) of 3,5-bis(trifluoromethyl)benzoyl chloride. The resulting yellow mixture was stirred cold for 30 minutes and the reaction was quenched with 50 ml of saturated aqueous sodium bicarbonate solution. The quenched mixture was partitioned between 300 ml of ether and 50 ml of water and the layers were separated. The organic layer was dried over magnesium sulfates. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid. $^1$H NMR (200 MHz, CDCl$_3$) δ2.50 (1H, dt, J=3.4, 12.0 Hz), 2.97 (1H, app d, J=12.0 Hz), 2.99 (1H, d, J=13.6 Hz), 3.72–3.79 (1H, m), 3.82 (1H, d, J=2.6 Hz), 4.00 (1H, d, J=13.6 Hz), 4.20 (dt, J=2.4, 11.6 Hz), 6.22 (1H, d, J=2.6 Hz), 7.22-7.37 (7H, m), 7.57 (2H, app d, J=6.8 Hz), 8.07 (1H, s), 8.47 (2H, s). MS (FAB) m/z 528 (M+H, 25%), 270 (100%).

Analysis Calcd. for C$_{26}$H$_{20}$F$_7$NO$_3$: C, 59.21; H, 3.82; N, 2.66; F, 25.21; Found: C, 59.06; H, 4.05; N, 2.50; F, 25.18%.

DESCRIPTION 4

4-Benzyl-2-(R)-(1-(3,5-bis(trifluoromethyl)phenyl)ethenyloxy)-3-(S)-(4-fluorophenyl)morpholine Step A: Dimethyltitanocene A solution of 2.49 g (10.0 mmol) of titanocene dichloride in 50 ml of ether in the dark at 0° C. was treated with 17.5 ml of 1.4M methyllithium solution in ether maintaining the internal temperature below 5° C. The resulting yellow/orange mixture was stirred at room temperature for 30 minutes and the reaction was quenched by slowly adding 25 g of ice. The quenched reaction mixture was diluted with 50 ml of ether and 25 ml of water and the layers were separated. The organic layer was dried over magnesium sulfate and concentrated in vacuo to afford 2.03 g (98%) of the title compound as a light-sensitive solid. The dimethyl titanocene could be stored as a solution in toluene at 0° C. for at least 2 weeks without apparent chemical degradation. $^1$H NMR (200 MHz, CDCl$_3$) δ−0.15 (6H, s), 6.06 (10H, s).

Step B: 4-Benzyl-2-(R)-(1-(3,5-bis(trifluoromethyl)phenyl)ethenyloxy)-3-(S)-(4-fluorophenyl)morpholine A solution of the compound of Description 3 (2.50 g, 4.9 mmol) and 2.50 g (12.0 mmol) of dimethyl titanocene (from Step A) in 35 ml of 1 liter v/v THF/toluene was stirred in an off bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. An analytical sample was obtained via recrystallisation from isopropanol: $^1$H NMR (400 MHz, CDCl$_3$) δ2.42 (1H, dt, J=3.6, 12.0 Hz), 2.90 (1H, app d, J=12.0 Hz), 2.91 (1H, d, J=13.6 Hz), 3.62–3.66 (1H, m), 3.72 (1H, d, J=2.6 Hz), 3.94 (1H, d, J=13.6 Hz), 4.09 (1H, dt, J=2.4, 12.0 Hz), 4.75 (1H, d, J=3.2 Hz), 4.82 (1H, d, J=3.2 Hz), 5.32 (1H, d, J=2.6 Hz), 7.09 (2H, t, J=8.8 Hz), 7.24–7.33 (5H, m), 7.58–7.62 (2H, m), 7.80 (1H, s), 7.90 (2H, s); MS (FAB) 526 (M+H, 75%), 270 (100%).

Analysis Calcd. for C$_{27}$H$_{22}$F$_7$NO$_2$: C, 61.72; H, 4.22; N, 2.67; F, 25.31; Found: C, 61.79; H, 4.10; N, 2.65; F, 25.27%.

DESCRIPTION 5

2-(R)-(1-(R)-(3,5-Bis(trifluoromethyl)phenyl)ethoxy)-3-(S)-(4-fluorophenyl)morpholine The compound of Description 4 (4.0 g) was dissolved in ethyl acetate (50 ml) and isopropanol (16 ml). To this solution was added palladium on charcoal (1.5 g) and the mixture was hydrogenated at 40 psi for 36 h. The catalyst was removed by filtration through Celite and the solvents were removed in vacuo. The residue was purified by flash chromatography on silica using 100% ethyl acetate and then 1–10% methanol in ethyl acetate. This afforded isomer A 500 mg (15%) and isomer B 2.6 g (80%) as clear oils -isomer B crystallised on standing. For the title compound: $^1$H NMR (400 MHz, CDCl$_3$) δ1.16 (3H, d, J=6.8 MHz), 1.80 (1H, br s), 3.13 (1H, dd, J=3.2, 12.4 Hz), 3.23 (1H, dt, J=3.6, 12.4 Hz), 3.63 (1H, dd, J=2.4, 11.2 Hz), 4.01 (1H, d, J=2.4 Hz), 4.13 (1H, dt, J=3.2, 12.0 Hz), 4.42 (1H, d, J=2.4 Hz) 4.19 (1H, q, J=6.8 Hz), 7.04–7.09 (2H, m), 7.27–7.40 (4H, m), 7.73 (1H, s); MS (FAB) 438 (M+H, 75%), 180 (100%).

HCl salt formation. To a solution of the free base (0.77 g) in diethyl ether (10 ml) was added 1M-HCl in methanol (1.75 ml). The solution was evaporated to dryness and on addition of diethyl ether crystals formed. The solution was filtered and the residue washed with diethyl ether to give the title compound hydrochloride salt mp 248°–250° C.

Analysis Calcd. for C$_{20}$H$_{18}$F$_7$NO$_2$.HCl: C, 50.70; H, 4.04; N, 2.96; Cl, 7.48; Found: C, 50.46; H, 3.85; N, 3.01; Cl, 7.31%.

DESCRIPTION 6

4-Benzyl-3-(S)-(4-fluorophenyl)-2-(R)-(3-fluoro-5-(trifluoromethyl)benzoyloxy)morpholine The title compound was prepared from the reaction of the compound of Description 2 with 3-fluoro-5-(trifluoromethyl)benzoyl chloride according to the procedure illustrated in Description 3. $^1$H NMR (360 MHz, CDCl$_3$) δ2.50 (1H, dt, J=3.3, 12.0 Hz), 2.96 (1H, d, J=12.0 Hz), 2.98 (1H, d, J=13.6 Hz), 3.75 (1H, dd, J=1.7, 11.5 Hz), 3.80 (1H, d, J=2.5 Hz), 3.92 (1H, d, J=13.6 Hz), 4.19 (1H, dt, J=2.1, 12.0 Hz), 6.20 (1H, d J=2.5 Hz), 6.99 (2H, t, J=8.7 Hz), 7.2–7.37 (5H, m), 7.51–7.55 (3H, m), (1H, d, J=8.4 Hz), 8.09 (1H, s). MS (CI$^+$) m/z 478 (M$^+$+1, 100%).

Analysis Calcd. for C$_{25}$H$_{20}$F$_5$NO$_3$: C, 62.88; H, 4.23; N, 2.93; Found: C, 62.59; H, 4.03; N, 3.07%.

DESCRIPTION 7

4-Benzyl-3-(S)-(4-fluorophenyl)-2-(R)-(1-(3-fluoro-5-(trifluoromethyl)phenyl)ethenyloxy)morpholine The title compound was prepared in 85% yield from the compound of Description 6 according to the procedure illustrated in Description 4. $^1$H NMR (360 MHz, CDCl$_3$) δ2.42 (1H, dr, J=3.6, 12.0 Hz), 2.90 (1H, d, J=12.0 Hz), 2.91

(1H, d, J=13.6 Hz), 3.60–3.62 (1H, m), 3.72 (1H, d, J=2.6 Hz), 3.92 (1H, d, J=13.6 Hz), 4.09 (1H, dt, J=2.4, 12.0 Hz), 4.67 (1H, d, J=2.9 Hz), 4.76 (1H, d, J=2.9 Hz), 5.28 (1H, d, J=2.6 Hz), 7.07 (2H, t, J=8.7 HHz), 7.2–7.37 (1H, m), 7.53 (1H, s), 7.57–7.61 (2H, m). MS (CI$^+$) 476 (M+1, 100%).

DESCRIPTION 8

3-(S)-(4-Fluorophenyl)-2-(R)-(1-(R)-(3-fluoro-5-(trifluoromethyl)phenyl)ethoxy)morpholine The compound of Description 7 was hydrogenated according to the method illustrated in Description 5. This afforded a mixture of 2 epimeric products isomer A and isomer B (the major product) as clear offs. For the title compound: $^1$H NMR (360 MHz, CDCl$_3$) δ1.42 (3H, d, J=6.6 Hz), 1.91 (1H, s), 3:11 (1H, dd, J=3.2, 12.4 Hz), 3.22 (1H, dt, J=3.6, 12.4 Hz), 3.58–3.62 (1H, m), 4.01 (1H, d, J=2.3 Hz), 4.11 (1H, dt, J=3.2, 12.0 Hz), 4.41 (1H d, J=2.3 Hz), 4.80 (1H, q, J=6.6 Hz), 6.41 (1H, d, J=9.2 Hz), 6.86 (1H, s), 7.02 (2H, t, J=8.7 Hz), 7.08 (2H, d, J=9.2 Hz), 7.21–7.26 (2H, m). MS (CI$^+$) m/z 387 (M+1, 100%).

Analysis Calcd. for C$_{19}$H$_{18}$F$_5$NO$_2$: C, 58.91; H, 4.69; N, 3.620; Found: C, 58.88; H, 4.81; N, 3.76%.

DESCRIPTION 9

2-(R)-(1-(R)-(3,5-Bis(trifluoromethyl)phenyl)ethoxy-4-(5-(dimethylaminomethyl)-1,2,3-triazol-4-yl)methyl-3-(S)-(4-fluorophenyl)morpholine

Method A a) 2-(R)-(1-(R)-(3,5-Bis(trifluoromethyl)phenyl)ethoxy-3-(S)-(4-fluorophenyl)-4-proparaylmorpholine Propargyl bromide (1.9 ml) was added to a stirred mixture of the compound of Description 5 (5 g) and potassium carbonate (4.76 g) in dry dimethylformamide at 23° C. After 15 min the reaction mixture was diluted with water (250 ml) and extracted with ethyl acetate (3×100 ml). The combined organic phases were washed with brine (1×100 ml) then dried (K$_2$CO$_3$) and concentrated to leave an oil. This was purified by chromatography on silica using ethyl acetate in hexane (1:9 then 1:4) as eluent to afford the title compound as an oil. $^1$H NMR (250 MHz, CDCl$_3$) δ1.50 (3H, d, J=6.6 Hz), 2.21 (1H, s), 2.84 (1H, d, J=11.1 Hz), 2.97 (1H, td, J=3.2, 11.7 Hz), 3.26 (2H, d, J=1.8 Hz), 3.62 (1H, d, J=2.2 Hz), 3.71 (1H, dd, J=2.3, 11.1 Hz), 4.33 (2H, m), 4.89 (1H, q, J=6.6 Hz), 7.03 (2H, t, J=8.6 Hz), 7.18 (2H, s), 7.38 (2H, br s), 7.63 (1H, s). MS (CI$^+$) m/z 476 (MH, 100%).

b) 2-(R)-(1-CR)-(3,5-Bis(trifluoromethyl)phenyl)ethoxy)-4-(4-dimethylamino-4-oxo-but-2-ynyl)-3-(S)-(4-fluorophenyl)morpholine A mixture of N,N-dimethylcarbamoyl chloride (0.195 ml), cuprous iodide (2mg), bis(triphenylphosphine)palladium (II) chloride (2 mg), triphenylphosphine (3mg) and the compound described in (a) above (1 g) in triethylamine (4 ml) was heated at 90° C. for 5 h in an inert atmosphere. The mixture was cooled to 23° C. and methanol (1 ml) was added and the solvent was removed in vacuo. The residue was partitioned between water and ethyl acetate and the layers were separated. The aqueous phase was extracted with ethyl acetate (2×20 ml). The combined organic phases were washed with water, brine, dried (MgSO$_4$) and concentrated to leave an off. The residue was purified by chromatography on silica using ethyl acetate in hexane (1:1) then ethyl acetate as eluant to provide the title compound as an oil. $^1$H NMR (250 MHz, CDCl$_3$) δ1.49 (3H, d, J=6.6 Hz), 2.84–3.06 (2H, m), 3.00 (3H, s), 3.17 (3H, s), 3.44 (2H, s), 3.64 (1H, br s), 3.73 (1H, dd, J=2.0, 11.1Hz), 4.33 (2H, m), 4.88 (1H, q, J=6.6 Hz), 7.03 (2H, t, J=8.7 Hz), 7.17 (2H, s), 7.38 (2H, br s), 7.63 (1H, s). MS (CI$^+$) m/z 547 (MH, 100%).

c) 2-(R)-(1-(R)-(3,5-Bis(trifluoromethyl)phenyl)ethoxy)-4-(5-N,N-dimethylcarboxamido-1,2,3-triazol-4-yl)methyl-3-(S)-(4fluorophenyl)morpholine A mixture of the compound described in (b) above (1.1 g) and sodium azide (0.65 g) in dimethylsulphoxide (7.5 ml) was heated at 70° C. for 17 h. The mixture was cooled to 23° C. and excess dimethylsulphoxide was removed by distillation in vacuo. The residue was partitioned between brine and ethyl acetate. The layers were separated and the organic layer was washed with brine (2×20 ml) then dried (MgSO$_4$) and concentrated to leave an oil. This was purified by chromatography on silica using ethyl acetate in hexane (1:2 then 1:1) and then ethyl acetate as eluent to provide the title compound as a pale yellow foam. $^1$H NMR (360 MHz, CDCl$_3$) δ1.47 (3H, d, J=6.6 Hz), 2.64 (1H, m), 2.90 (1H, d, J=11.6 Hz), 3.09 (3H, s), 3.34 (3H, s), 3.65 (3H, m), 3.92 (1H, d, J=15.5 Hz), 4.27 (1H, td, J=2.1, 9.5 Hz), 4.35 (1H, d, J=2.6 Hz), 4.89 (1H, q, J=6.6 Hz), 7.01 (2H, t, J=8.7 Hz), 7.16 (2H, s), 7.39 (2H, br s), 7.64 (1H, s). m/z 590 (MH, 100%).

d) 2-(R)-(1-(R)-3,5-Bis(trifluoromethyl)phenyl)ethoxy)-4-(5-(dimethylaminomethyl)-1,2,3-triazol-4-yl)methyl-3-(S)-(4-fluorophenyl)morpholine Lithium aluminium hydride (0.47 ml, 1M in tetrahydrofuran) was added dropwise to a solution of the compound described in (c) above (0.11 g) in dry tetrahydrofuran (1 ml) under an inert atmosphere at 23° C. After 30 min sodium hydroxide (10 drops, 1M) was added followed by water (5 drops). Ethyl acetate (50 ml) was then added and the resulting mixture was filtered through a pad of Hyfio™. The filtrate was concentrated in vacuo and the residue was purified by chromatography on silica using ethyl acetate in methanol (9:1 then 4:1) as eluant to provide the title compound as a foam. $^1$H NMR (360 MHz, CDCl$_3$) δ1.44 (3H, d, J=6.6 Hz), 2.25 (6H, s), 2.57 (1H, td, J=3.4, 8.55 Hz), 2.90 (1H, d, J=11.7 Hz), 3.25 (1H, d, J=14.0 Hz), 3.43 (1H, d, J=13.6 Hz), 3.45 (1H, d, J=2.2 Hz), 3.53 (1H, d, J=13.6 Hz), 3.61 (1H, d, J=11.2 Hz), 3.78 (1H, d, J=14.0 Hz), 4.22 (1H, t, J=9.3 Hz), 4.32 (1H, d, J=2.2 Hz), 4.86 (1H, q, J=6.6 Hz), 7.06 (2H, t, J=8.7 Hz), 7.16 (2H, s), 7.48 (2H, br s), 7.63 (1H,s). m/z 576 (MH).

Method B

2-(R)-1-(R)-(3,5-Bis(trifluoromethyl)phenyl)ethoxy)-3-(S)-(4-fluorophenyl)-4-(4-chlorobut-2-ynyl)morpholine a) A solution of the product of Description 5 (free base, 5 g) in N,N-dimethylformamide (20 ml) was slowly added to a heated (50° C.) solution of 1,4-dichlorbut-2-yne (2.2 ml) and potassium carbonate (4.8 g) in N,N-dimethylformamide (20 ml). The solution was heated for a further 5 h at 50° C. and then the solvent removed in vacuo. To the residue was added water (400 ml) and the product extracted into ethyl acetate (3×150 ml). The combined organic phase washed with water, saturated brine and dried (MgSO$_4$). The solvent was removed in vacuo and the residue chromatographed on silica gel (eluting with 10% ethyl acetate in petroleum ether bp 60°–80° C.) to give the title compound. $^1$H NMR (250 MHz, CDCl$_3$) δ1.41 (3H, d, J=6.6 Hz), 2.80 (1H, app. t, J=10.8 Hz), 2.87 (1H, td, J=3.5, 11.7 Hz), 3.22 (2H, t, J=1.9 Hz), 3.52 (1H, d, J=2.8 Hz), 3.68 (1H, d, J=1.4 Hz, 11.1 Hz), 4.00 (2H, t, J=1.9 Hz), 4.22–4.32 (2H, m), 4.81 (1H, q, J=6.6 Hz), 6.96 (2H, t, J=8.7 Hz), 7.10 (2H, s), 7.31 (2H, br s), 7.56 (1H, s). m/z (CI$^+$) 524 (M+H, 100%).

b) N-(4-Azidobut-2-ynyl)-2-(R)-(1-(R)-(3,5-bis(trifluoromethyl)phenyl)ethoxy)-3-(S)-(4-fluorophenyl)morpholine To a solution of 2-(R)-(1-(R)-(3,5-bis(trifluoromethyl)phenyl)ethoxy)-3-(S)-(4-fluorophenyl)-4-(4-chlorobut-2-ynyl)morpholine (4 g) in dimethyl sulphoxide (17 ml) was added sodium azide (0.562 g). The solution was stirred for 20 h and aqueous ammonium chloride and ethyl acetate were added. The organic phase was washed with water (2 times), saturated brine and dried (MgSO$_4$). The solvent was removed in vacuo and the residue chromatographed on silica gel (eluting with 20% ethyl acetate in petroleum ether bp 60°–80° C.) to give the title compound. $^1$H NMR (360 MHz, CDCl$_3$) δ1.48 (3H, s, J=6.6 Hz), 2.87 (1H, app t, J=10.2 Hz), 2.98 (1H, td, J=3.6, 11.7 Hz), 3.35 (2H, t, J=1.9 Hz), 3.61 (1H, d, J=2.8 Hz), 3.72 (1H, dq, J=1.4 Hz, 10.0 Hz), 3.92 (2H, t, J=1.9 Hz), 4.30–4.40 (2H, m), 4.89(1H, q, J=6.6 Hz), 7.03 (2H, t, J=8.7 Hz), 7.17 (2H, s), 7.27 br s), 7.63 (1H, s).

c) 2-(R)-(1-(R)-3,5-Bis(trifluoromethyl)phenyl)ethoxy)-4-(5-(dimethylaminomethyl)-1,2,3-triazol-4-yl)methyl-3-(S)-(4-fluorophenyl)morpholine Dimethylamine (approximately 10 ml) was condensed at −80° C. in a pressure tube and to this was added a solution of N-(4-azidobut-2-ynyl)-2-(R)-(1-(R)-(3,5-bis(trifluoromethyl)phenyl)ethoxy)-3-(S)-(4-fluorophenyl)morpholine (3.2 g) in dioxan (15 ml). The tube was sealed and the solution was heated at 90° C. for 16 h. The solution was evaporated to dryness and the residue chromatographed on silica gel (eluting with 5% methanol in dichloromethane containing 0.25% ammonia (SG. 0.88)) and the fractions containing the desired product were evaporated in vacuo to give the title compound. To a solution of this residue in diethyl ether was added 1M-HCl in methanol. The solution was evaporated to dryness and redissolved in diethyl ether to give crystals of the title compound hydrochloride salt m.p. 194°–198° C., [α]$^{22}_D$+65.0° (c=0.5, H$_2$O). The crystals were found to be stable for at least five days at 40° C.; at 40° C./75% relative humidity; at 80° C.; and at 2000LUX.

DESCRIPTION 10

3-(S)-(4-Fluorophenyl)-2-(R)-(1-(R)-(3-fluoro-5-(trifluoromethyl)phenyl)ethoxy)-4-(5-pyrrolidinomethyl-1,2,3-triazol-4-yl)methylmorpholine The title compound was preapred from the compound of Description 8 according to the method of Description 9, Method B, via the corresponding N-(4-azidobut-2-ynyl) morpholine and pyrrolidine. $^1$H NMR (360 MHz, CDCl$_3$) δ1.40 (3H, d, J=6.6 Hz), 1.81 (4H, br s), 2.53–2.61 (5H, m), 2.89 (1H, d, J=11.7 Hz), 3.27 (1H, d, J=14.0 Hz), 3.45 (1H, d, J=2.8 Hz), 3.63 (1H, m), 3.63 (1H, d, J=13.7 Hz), 2.59–3.63 (1H, m), 3.63 (1H, d, J=13.7 Hz), 3.73 (1H, d, J=13.7 Hz), 3.83 (1H, d, J=14.0 Hz), 4.21 (1H, dt, J=11.6, 2.1 Hz), 4.32 (1H, d, J=2.8 Hz) (1H, q, J=6.6 Hz), 6.37 (1H, d, J=9.1 Hz), 6.80 (1H, s), 7.05–7.10 (3H, m), 7.46 (2H, br s). MS (CI$^+$) 552 (M+1, 100%).

DESCRIPTION 11

3-(S)-(4-Fluorophenyl)-2-(R)-(1-(R)-(3-methylthio-5-(trifluoromethyl)phenyl)ethoxy)-4-(5-pyrrolidinomethyl-1,2,3-triazol-4-yl)methylmorpholine The compound of Description 10 (0.5 mmol) was heated to 120° C. with sodium thiomethoxide (2.5 mmol) in anhydrous DMF (10 ml) for between 2–5 hours. The cooled solution was diluted with water (150 ml), extracted with ethyl acetate (4×40 ml), dried (MgSO$_4$) and concentrated in vacuo to a crude off which was purified by flash silica gel chromatography in 5–10% methanol/dichloromethane to yield the title compound as a foam (620 mg, 81%). $^1$H NMR (360 MHz,CDCl$_3$) δ1.40 (3H, d, J=6.6 Hz), 1.79 (4H, br s), 2.36 (3H, s), 2.5–2.6 (3H, m), 2.87 (1H, d, J=11.7 Hz), 3.23 (1H, d, J=13.9 Hz), 3.43 (1H, d, J=2.8 Hz), 3.57–3.64 (2H, m), 3.71 (1H, d, J=13.7 Hz), 3.78 (1H, d, J=14.0 Hz), 4.21 (1H, m), 4.33 (1H, d, J=2.8 Hz), 4.74 (1H, q, J=6.5 Hz), 6.71 (2H, s), 7.06 (2H, t, J=8.7 Hz), 7.19 (1H, s), 7.47 (2H, br s); MS (ES$^+$) m/z 580 (M+1, 100%).

EXAMPLE 1

2-(R)-(1-(R)-(3,5-Bis(trifluoromethyl)phenyl)ethoxy)-3-(S)-(4-fluorophenyl)-4-(5-(N,N-dimethylamino(N-oxide)methyl)-1,2,3-triazolyl)methylmorpholine To a heated (60° C.) solution of 2-(R)-(1-(R)-(3,5-bis(trifluoromethyl)phenyl)ethoxy)-3-(S)-(4-fluorophenyl)-4-(5-(N,N-dimethylaminomethyl)-1,2,3-triazol-4-yl)methylmorpholine (Description 9) (0.245 g, 0.442 mmol) dissolved in soya bean oil (6 ml) was added a 30% solution of aqueous hydrogen peroxide (0.2 ml) in portions over 4 h. The solution was then cooled to room temperature for 16 hours and the resulting suspension applied to a column containing silica and the products eluted with a gradient between dichloromethane and a mixture of dichloromethane:methanol:aqueous ammonia solution (200:50:1). This crude product was recrystallised from aqueous ethanol to give the title compound mp 139°–140° C. m/z (CI$^+$) 592 (M+H).

Analysis Calcd. for C$_{26}$H$_{28}$F$_7$N$_5$O$_3$. 0.8H$_2$O: C, 51.54; H, 4.92; N, 11.56; Found: C, 51.52; H, 4.71; N, 11.21%

$^1$H NMR (360 MHz, CH$_3$OH-d$_4$) δ1.47 (3H, d, J=6.58 Hz), 2.54 (1H, td), 2.78 (1H, d, J=11.95 Hz), 3.10 (3H, s), 3.15 (3H, s), 3.35 (1H, AB d, J=14.49 Hz), 3.50 (1H, d), 3.63 (1H, br d, J=11.53 Hz), 3.82 (1H, AB d, J=14.5 Hz), 4.23 (1H, td), 4.29 (1H, AB d, J=13.55 Hz), 4.36 (1H, d, J=2.69 Hz), 4.49 (1H, AB d, J=13.43 Hz), 4.96 (1H, q, J=6.48 Hz), 7.08 (2H, t, J=8.7 Hz), 7.35 (2H, s), 7.56 (2H, br t), 7.71 (1H, s).

EXAMPLE 2

2-1-(R)-(1-(R)-(3,5-Bis(trifluoromethyl)phenyl)ethoxy)-3-(S)-(4-fluorophenyl)-4-(5-(N,N-dimethylaminomethyl)-1,2,3-triazol-4-yl)methylmorpholine 1-loxide To a solution of 2-(R)-(1-(R)-(3,5-bis(trifluoromethyl)phenyl)ethoxy)-3-(S)-(4-fluorophenyl)-4-(5-(N,N-dimethylaminomethyl)-1,2,3-triazol-4-yl)methylmorpholine (Description 9) (0.245 g, 0.442 mmol) dissolved in dichloromethane (3.6 ml) and acetic acid (1.81 ml) was added a solution of 30% aqueous hydrogen peroxide (0.368 ml). The solution was stirred at room temperature for 16 hours and was then chromatographed on silica gel eluting with a gradient between chloroform and a mixture of chloroform:methanol:acetic acid:water (800:200:30:3) and then chromatographed on silica gel eluting with a gradient between dichloromethane and a mixture of dichloromethane:methanol:aqueous ammonia solution (200:50:1), to give, after evaporation and washing with hexane, the title compound mp 132°–134° C. m/z (CI$^+$) 592 (M+H).

Analysis Calcd. for C$_{26}$H$_{28}$F$_7$N$_5$O$_3$. 1.3H$_2$O: C, 50.78; H, 5.02; N, 11.39; Found: C, 50.67; H, 5.05; N, 11.15%

$^1$H NMR (360 MHz, CH$_3$OH-d$_4$) δ1.59 (3H, d, J=6.59 Hz), 2.90 (1H, d, 12.95 Hz), 3.78 (2H, m), 3.90 (1H, AB d, J=13.41 Hz), 4.00 (1H, AB d, J=13.59 Hz), 4.06 (1H, AB d, J=13.21 Hz), 4.50 (1H, AB d, J=13.26 Hz), 4.71 (1H, d, J=3.56 Hz), 4.89 (1H, d, J=3.61 Hz), 5.00 (1H, q, J=6.47 Hz), 7.15 (2H, t, J=8.28 Hz), 7.62 (2H, s), 8.0 (2H, vbr s), 7.76 (1H, s).

EXAMPLE 3

2-(R)-(1-(R)-(3,5-Bis(trifluoromethyl)phenyl)ethoxy)-3-(S)-(4-fluorophenyl)-4-(5-(N,N-dimethylamino(N-oxide)methyl)-1,2,3-triazol-4-yl)methylmorpholine N-oxide From the chromatographic separation described in Example 1 was isolated the title compound m/z (CI$^+$) 608 (M+H).

EXAMPLE 4

3-(S)-(4-Fluorophenyl)-2-(R)-(1-(R)-(3-methylthio-5-(trifluoromethyl)phenyl)ethoxy)-4-(5-pyrrolidinomethyl-1,2,3-triazol-4-yl)methylmorpholine N-oxide The thioether of Description 11 (557 mg, 0.96 mmol) was dissolved in chloroform (10 ml) and cooled to −24° C. m-Chloroperoxybenzoic acid (80–85%, 207 mg, 0.96 mmol) was added quickly in portions and the reaction mixture stirred at this temperature for 1 hour before warming to room temperature. The resulting solution was diluted with chloroform (20 ml), washed with sodium bicarbonate solution (30 ml, 0.5M), dried (MgSO$_4$) and concentrated in vacuo. The crude concentrate was purified by flash silica gel chromatography eluting with dichloromethane/methanol/concentrated aqueous ammonia (91:8:1 to 86:12:2) to yield in order, recovered started material (143 mg, 26%); the title compound (morpholine N-oxide) (121 mg, 21%); and the bis(N-oxide) (Example 5) (153 mg, 26%), all as foams.

Analysis Calcd. for $C_{28}H_{33}F_4N_5O_3S\cdot2H_2O$: C, 53.24; H, 5.90; N, 11.09; Found: C, 53.24; H, 5.74; N, 10.76%

$^1$H NMR (360 MHz, CDCl$_3$) δ1.41 (3H, d, J=6.5 Hz), 1.90 (4H, br s), 2.28 (3H, s), 2.70–2.80 (2H, m), 2.84 (1H, d, J=12.6 Hz), 2.90–3.00 (2H, m), 3.59 (1H, d, J=12.0 Hz), 3.80 (1H, d, J=13.0 Hz), 3.80–3.88 (1H, m), 3.90 (1H, d, J=13.1 Hz), 3.98 (1H, d, J=13.0 Hz), 4.61–4.71 (3H, m), 4.87 (1H, d, J=2.6 Hz), 4.89 (1H, m), 6.87 (2H, s), 7.00 (2H, br t, J=8.1 Hz), 7.16 (1H, s), 7.6–8.2 (~2H, vbr s); MS (ES$^+$) 596 (M+1. 100%); HPLC 96–98% pure.

EXAMPLE 5

3-(S)-(4-Fluorophenyl)-2-(R)-(1-(R)-(3-methylthio-5-(trifluoromethyl)phenyl)ethoxy)-4-(5-pyrrolidino(N-oxide)methyl-1,2,3-triazol-4-yl)methylmornholine N-oxide From the chromatography described in Example 4. $^1$H NMR (360 MHz, CDCl$_3$) δ1.45 (3H, d, J=6.6 Hz), 1.90–2.40 (4H, br m), 2.28 (3H, s), 3.24 (1H, d, J=12.9 Hz), 3.35 (1H, m), 3.56–3.85 (5H, br m), 4.08 (1H, d, J=13.0 Hz), 4.50 (1H, d, J=13.1 Hz), 4.56–4.71 (3H, m), 4.83 (1H, d, J=13.1 Hz), 5.04 (1H, d, J=3.4 Hz), 5.13 (1H, d, J=13.0 Hz), 6.89 (2H, s), 6.99 (2H, br t), 7.16 (1H, s), 7.6–8.2 (~2H, vbr s); MS (ES$^+$) 612 (M+1, 100%).

What we claim is:
1. A compound of the formula (I):

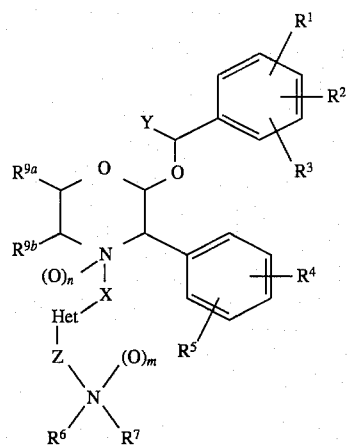

wherein $R^1$ is hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, $CF_3$, $OCF_3$ or $C_{1-6}$alkoxy substituted by $C_{1-4}$alkoxy;

$R^3$ is hydrogen, halogen, $CF_3$ or $OCF_3$;

$R^4$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, $C_{1-6}$alkoxy substituted by $C_{1-4}$alkoxy or $CF_3$;

$R^6$ is hydrogen, $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxy;

$R^7$ is hydrogen, $C_{1-4}$alkyl, $C_{3-7}$cycloalkyl, $C_{3-7}$cycloalkyl$C_{1-4}$alkyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;

or $R^6$ and $R^7$, together with the nitrogen atom to which they are attached, form a saturated or partially saturated heterocyclic ring of 4 to 7 ring atoms, which ring may optionally contain in the ring one oxygen or sulphur atom or a group selected from $NR^8$, S(O) or S(O)$_2$ and which ring may be optionally substituted by one or two groups selected from hydroxy, $C_{1-4}$alkyl, hydroxy$C_{1-4}$alkyl, $C_{1-4}$alkoxy$C_{1-4}$alkyl, oxo, $COR^a$ or $CO_2R^a$ where $R^a$ is as previously defined;

or $R^6$ and $R^7$ together with the nitrogen atom to which they are attached, form a non-aromatic azabicyclic ring system of 6 to 12 ring atoms;

or Z, $R^6$ and the nitrogen atom to which they are attached form a heteroaliphatic ring of 4 to 7 ring atoms which may optionally contain an oxygen ring atom;

$R^8$ is hydrogen, $C_{1-4}$alkyl, hydroxy$C_{1-4}$alkyl or $C_{1-4}$alkoxy$C_{1-4}$alkyl;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

Het is a 5- or 6-membered heterocyclic ring containing 2 or 3 nitrogen atoms optionally substituted by =O, =S or a $C_{1-4}$alkyl group;

X is an alkylene chain of 1 to 4 carbon atoms optionally substituted by oxo;

Y is a $C_{1-4}$alkyl group optionally substituted by hydroxy;

Z is $C_{1-6}$alkylene or $C_{3-7}$cycloalkylene;

m is 0 or 1; and n is 0 or 1, where the sum total of n+m is 1 or 2;

or a pharmaceutically acceptable salt thereof.

2. A compound as claimed in claim 1 wherein $R^1$ is hydrogen, $C_{1-4}$alkyl, $C_{1-4}$alkoxy, halogen or $CF_3$.

3. A compound as claimed in claim 1 wherein $R^2$ is hydrogen, $C_{1-4}$alkyl, $C_{1-4}$alkoxy, halogen or $CF_3$.

4. A compound as claimed claim 1 wherein $R^3$ is hydrogen, fluorine, chlorine or $CF_3$.

5. A compound as claimed in claim 1 wherein m is 1.

6. A compound of the formula (Ia) or a pharmaceutically acceptable salt thereof:

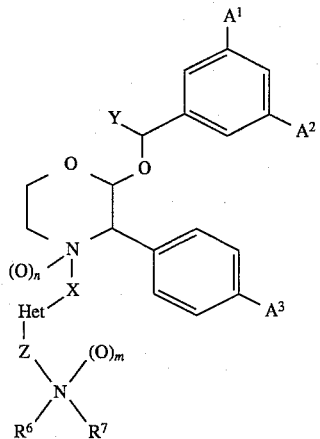

(Ia)

wherein $A^1$ is fluorine or $CF_3$;

$A^2$ is fluorine or $CF_3$;

$A^3$ is fluorine or hydrogen;

and $R^6$, $R^7$, X, Y, Z, Het, m and n are as defined in claim 1.

7. A compound as claimed in claim 1 wherein Y is a $C_{1-4}$alkyl group.

8. A compound as claimed in claim 1 wherein X is $CH_2$, $CH(CH_3)$ or $CH_2CH_2$.

9. A compound as claimed in claim 1 wherein the group Het-ZN(O)$_m$R$^6$R$^7$ is selected from:

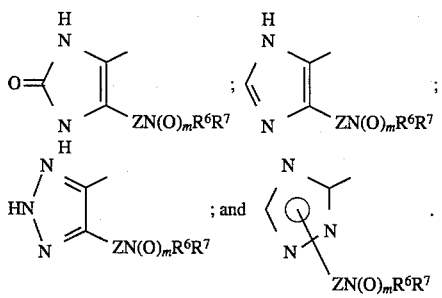

10. A compound as claimed in claim 9 wherein the group Het-ZN(O)$_m$R$^6$R$^7$ is:

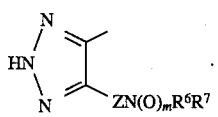

11. A compound a claimed in claim 1 wherein Z is $CH_2$ or $CH_2CH_2$ and $NR^6R^7$ is amino, methylamino, dimethylamino, diethylamino, azetidinyl, pyrrolidino and morpholino.

12. A compound selected from:

2-(R)-(1-(R)-(3,5-bis(trifluoromethyl)phenyl)ethoxy)4-(5-(N,N-dimethylamino(N-oxide)methyl)-1,2,3-triazol-4-yl)methyl-3-(S)-(4-fluorophenyl)morpholine;

2-(R)-(1-(R)-(3,5-bis(trifluoromethyl)phenyl)ethoxy)-4-(5-(N,N-dimethylaminomethyl)-1,2,3-triazol-4-yl)methyl-3-(S)-(4-fluorophenyl)morpholine N-oxide;

2-(R)-(1-(R)-(3,5-bis(trifluoromethyl)phenyl)ethoxy)-4-(5-(N,N-dimethylamino(N-oxide)methyl)-1,2,3-triazol-4-yl)methyl-3-(S)-(4-fluorophenyl)morpholine N-oxide;

3-(S)-(4-fluorophenyl)-2-(R)-(1-(R)-(3-methylthio-5-(trifluoromethyl)phenyl)ethoxy)-4-(5-pyrrolidinomethyl-1,2,3-triazol-4-yl)methylmorpholine N-oxide;

3-(S)-(4-fluorophenyl)-2-(R)-(1-(R)-(3-methylthio-5-(trifluoromethyl)phenyl)ethoxy)-4-(5-pyrrolidino(N-oxide)methyl-1,2,3-triazol-4yl)methylmorpholine N-oxide;

or a pharmaceutically acceptable salt thereof.

13. A pharmaceutical composition comprising a compound as claimed in claim 1 in association with a pharmaceutically acceptable carrier or excipient.

14. A method for the treatment of physiological disorders associated with an excess of tachykinins, which method comprises administration to a patient in need thereof of a tachykinin reducing amount of a compound according to claim 1, or a pharmaceutically acceptable salt thereof, or a composition comprising a compound according to claim 1, or a pharmaceutically acceptable salt thereof.

15. A method according to claim 14 for the treatment of pain or inflammation.

16. A method according to claim 14 for the treatment of migraine.

17. A method according to claim 14 for the treatment of emesis.

18. A method according to claim 14 for the treatment of postherpetic neuralgia.

19. A process for the preparation of a compound as claimed in claim 1 which comprises:

oxidation of one or both of the nitrogen atoms drawn in formula (II):

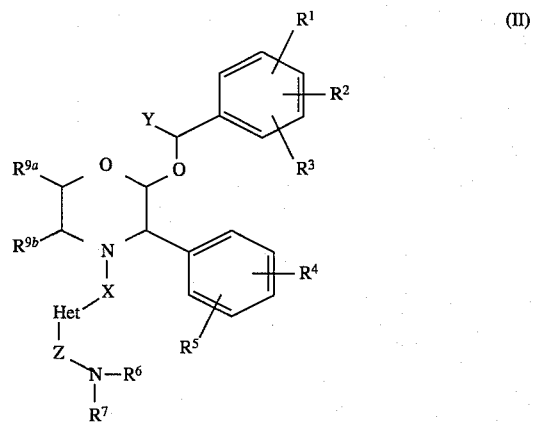

(II)

said process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

* * * * *